United States Patent [19]

Bradshaw et al.

[11] Patent Number: 4,858,623

[45] Date of Patent: Aug. 22, 1989

[54] ACTIVE FIXATION MECHANISM FOR LEAD ASSEMBLY OF AN IMPLANTABLE CARDIAC STIMULATOR

[75] Inventors: James I. Bradshaw, Surfside; Ross G. Baker, Jr., Houston, both of Tex.

[73] Assignee: Intermedics, Inc., Angleton, Tex.

[21] Appl. No.: 72,746

[22] Filed: Jul. 13, 1987

[51] Int. Cl.[4] .............................................. A61N 1/00
[52] U.S. Cl. ................................. 128/785; 128/419 P
[58] Field of Search ............... 128/419 D, 419 P, 786, 128/785, 784, 742, 698

[56] References Cited

U.S. PATENT DOCUMENTS

| | | | |
|---|---|---|---|
| 3,120,227 | 2/1964 | Hunter, Jr. et al. | 128/698 |
| 3,719,190 | 3/1973 | Avery | 128/785 |
| 3,800,784 | 4/1974 | Kiszel et al. | 128/642 |
| 3,814,104 | 6/1974 | Irnich et al. | 128/419 P |
| 3,989,038 | 11/1976 | Neward | 128/642 |
| 4,011,875 | 3/1977 | Lehr et al. | 128/785 |
| 4,103,690 | 8/1978 | Harris | 128/786 |
| 4,151,835 | 5/1979 | Showell et al. | 128/642 |
| 4,233,992 | 11/1980 | Bisping | 128/786 |
| 4,254,764 | 3/1981 | Neward | 128/642 |
| 4,294,258 | 10/1981 | Bernard | 128/642 |
| 4,378,023 | 3/1983 | Trabucco | 128/785 |
| 4,649,938 | 3/1987 | McArthur | 128/785 |
| 4,660,571 | 4/1987 | Hess et al. | 128/786 |

FOREIGN PATENT DOCUMENTS

| | | | |
|---|---|---|---|
| 2907135 | 8/1980 | Fed. Rep. of Germany | 128/419 P |
| 3146182 | 11/1981 | Fed. Rep. of Germany | 128/419 P |
| 3415410 | 10/1984 | Fed. Rep. of Germany | 128/419 P |
| 2099307 | 12/1982 | United Kingdom | 128/419 P |

OTHER PUBLICATIONS

P Wave Synchronous Pacing Using Anchored Atrial Electrode Implanted Without Thoracotomy, The American Journal of Cardiology, vol. 30, Jul. 11, 1972, pp. 74-76.

Primary Examiner—Franics Jaworski
Assistant Examiner—George Manuel
Attorney, Agent, or Firm—John R. Merkling

[57] ABSTRACT

An active fixation mechanism for a pacemaker lead with a tissue-stimulating electrode has a rigid hook for engaging tissue pivotally fastened to the lead in the vicinity of the electrode. The tip of the hook is normally resiliently urged into a recess in the lead adjacent to the electrode. A mechanism is coupled to the lead to permit the normal bias on the hook tip to be selectively overcome to position the hook outwardly of the lead. In this position, the hook is deployed to engage tissue in the vicinity of the electrode. The force applied to deploy the hook may be removed to allow the hook to move back into the recess under the normal bias. Sufficient force applied to the hook while deployed, along the axis of the lead, will cause the hook to assume a position beyond the distal end of the lead, in which it is precluded from engaging tissue.

10 Claims, 1 Drawing Sheet

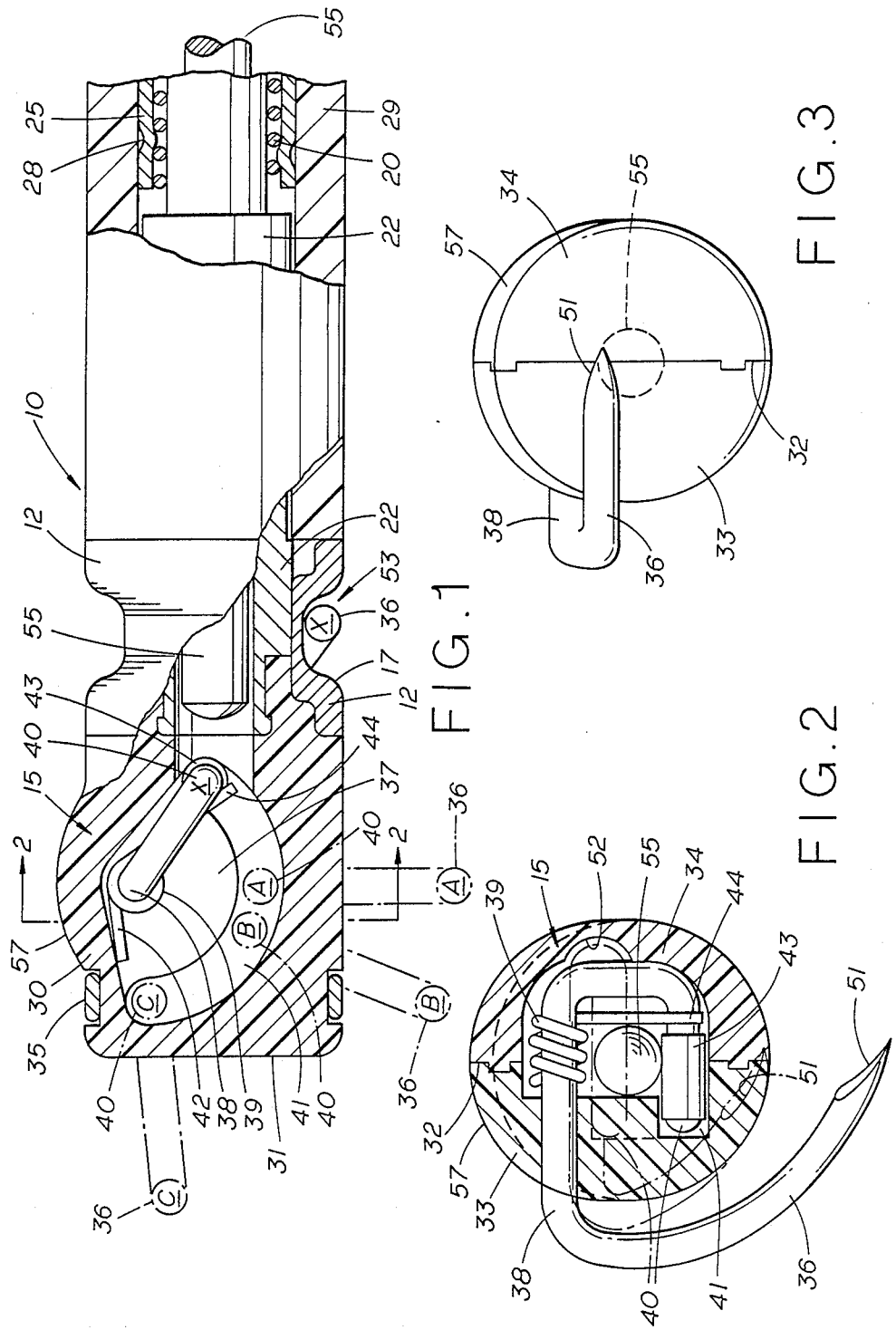

ACTIVE FIXATION MECHANISM FOR LEAD ASSEMBLY OF AN IMPLANTABLE CARDIAC STIMULATOR

BACKGROUND OF THE INVENTION

1. Field of the Invention

The present invention relates generally to implantable cardiac stimulators, such as cardiac pacemakers, cardioverters and defibrillators; and more particularly to fixation mechanisms for the lead/electrode assemblies of implantable cardiac stimulators.

2. Prior Art

The sinoatrial (S-A) node of the human heart acts as the natural pacemaker by which rhythmic electrical excitation is developed and propagated to the atria. In response, the atrial chambers contract, pumping blood into the ventricles. The rhythmic excitation is further propagated through the atrioventricular (A-V) node, which imposes a delay, and then via the conduction system consisting of the bundle of His and the Purkinge fibers to the ventricular myocardium, producing contraction of the ventricles. As a result, the oxygen-depleted blood in the right ventricle is pumped through the pulmonary artery to the lungs, and the oxygenated blood in the left ventricle is pumped through the arteries to the body. The right atrium receives the oxygen-depleted blood from the body via the veins, and the left atrium receives oxygenated blood from the lungs.

The actions repeat in a rhythmic cardiac cycle in which the atrial and ventricular chambers alternately contract and pump, relax and fill. One way valves along the veins, between the chambers in the right side (tricuspid valve) and the left side (mitral valve) of the heart, and at the exits of the right ventricle (pulmonary valve) and left ventricle (aortic valve) prevent backflow of the blood as it moves through the heart and circulatory system.

The S-A node is spontaneously rhythmic, and with a normal excitation and propagation system the heart beats in an organized manner at a regular rate termed sinus rhythm. Disruption of the natural pacing and propagation system as a result of aging or disease is commonly treated by artificial cardiac pacing, in which a cardiac pacemaker is implanted to maintain the desired heart rate.

Implantable artificial cardiac pacemakers, or, more simply, "pacemakers," are designed to operate in one of several different response modes. These include asynchronous, or fixed rate stimulation; inhibited, or stimulation only after a predetermined interval without specified normal cardiac activity; and triggered, or stimulation only in response to specified cardiac activity. All three of these pacemaker types employ, in simplest form, a stimulus generator ("pulse generator") housed in a case and powered by a self-contained battery, and a lead assembly (generally referred to simply as a "lead") having one or more electrodes coupled to conductor(s) for electrical connection to the generator circuitry via a connector built into the case. The pacing electrode is variously referred to as the stimulating cathodic electrode, the stimulating electrode, or merely the cathode, and the indifferent electrode is alternatively referred to as the reference electrode, the anodic electrode, or simply the anode. In fact, however, electrical activity takes place at each electrode during pacing, and the coupling may be such that each electrode acts, at different times, as cathode or anode. The pulse generator and the lead are manufactured and distributed as separate items, the leads being interchangeable with pulse generators of the various types.

Typically, the lead is inserted through the superior vena cava (the great vein which transports unoxygenated blood from the upper part of the body to the right atrium) until the stimulating electrode at the distal end of the lead is brought into proper position within the desired chamber in the right side of the patient's heart. Because it is adapted for intravenous insertion, the lead is sometimes referred to as a "catheter lead"; and because the electrode is adapted to be positioned within the heart, it is often called an "endocardial electrode". The proximal end of the lead is inserted and fastened into the integral connector of the pulse generator case, thereby electrically coupling the stimulating electrode to the pacemaker circuitry within the case. The case in which the pulse generator is housed is implanted in a subcutaneous pouch formed by an incision in the patient's chest. With dual chamber pacemakers, both chambers of the heart may be stimulated and/or sensed using two separate leads, one of which is introduced into the right atrium and the other into the right ventricle.

By appropriately manipulating the lead, the implanting physician positions and, if necessary, repositions the stimulating electrode to assure consistent "capture" of the heart, that is to say, that the patient's heart responds to each stimulus generated by the pacemaker. In essence, the stimulating electrode serves to impress an electric field, resulting from electrical discharge by the pulse generator, on excitable myocardial tissue in the vicinity of that electrode. This is accomplished via an electrical circuit consisting of the pulse generator, the conducting lead, the stimulating electrode, the indifferent electrode, and the volume conductor comprising the patient's body tissue and fluid.

The pacemaker may be arranged for unipolar or bipolar stimulation according to the configuration and location of the indifferent electrode. For unipolar stimulation, the anode is somewhat remote from the heart, typically constituting part of the metal case that houses the pulse generator. Some patients may experience pectoral stimulation as the heart is being paced, a condition attributable to the presence of a large area electrode—the case—in contact with the chest muscle. To alleviate that condition, it is customary to reduce the size of the anode to a small portion of the case itself by coating most of the case with a biologically compatible electrical insulator, such as paralene, leaving only the limited uncoated portion in conductive contact with the body tissue and fluid. This reduction in size of the anode may reduce the effectiveness of the circuit ground (reference potential). For such reasons, the cardiologist or surgeon may prefer to forego the simplicity of unipolar pacing for a particularly sensitive patient, and instead select bipolar pacing. for purposes of pacemaker operation in the latter mode, the lead to be implanted is configured with the cathode and the anode insulatively separated from but in close proximity to one another at the distal end of the lead. Typically, the cathode is located at or near the tip of the lead and the anode is configured as a ring electrode spaced back one half inch or so from the cathode. Each electrode is connected to its own electrically conductive coil within the lead.

The stimulating electric field generated by the pacemaker in the vicinity of the cathode must be of sufficient impulse strength to initiate a so-called "action potential" and depolarization of cells within the excitable tissue, in order to cause and propagate cardiac stimulation. The smallest electrical impulse necessary to initiate such stimulation is referred to as the "stimulation threshold," or simply "threshold".

In practice, the cardiologist or surgeon will set the stimulation level to comfortably exceed the threshold for the particular patient and pacing system. Indeed, since there is invariably an acute but gradual rise in threshold over a period of from about one to four weeks after the pacemaker is implated, it is customary to set the stimulus level initially at about four times that of the threshold measured at implant. The increase in acute threshold is attributable in part to the growth of a fibrotic layer of non-excitable tissue of uneven thickness about the electrode tip in contact with the myocardium, which effectively increases the surface area of the electrode and lowers the current density. Another factor is the inflammation reaction at the tip. The chronic threshold is usually observed about four to eight weeks after implantation.

It is common practice to seek to position the stimulating cathodic electrode at the time of implant at a location within the chamber to be paced which offers the lowest threshold and the greatest mechanical stability. Until the stimulating electrode becomes secured in place as a result of fibrotic growth, a period which depends in large measure on the structure and composition of the electrode, it is subject to dislodgement because of the rhythmic contraction and relaxation of the heart, or even merely as a consequence of general body movements of the patient.

Various electrode fixation mechanisms have been devised since the inception of the artificial pacemaker to secure the lead (and more particularly, the electrode) in place after positioning by the cardiologist or surgeon. Such mechanisms fall into two categories. Some offer passive fixation, by means of non-invasive devices such as pliant barbs (so-called "tines") attached at or near the lead tip to engage the trabeculae within the heart chamber. Others provide more positive fixation, termed "active fixation," of the electrode. The known active fixation mechanisms include corkscrews, hooks, piercing barbs, or other anchoring means arranged at or near the lead tip for penetration of the endocardium upon manipulation of the lead and/or a stylet traversing the lead, following proper positioning of the cathode.

It is a principal object of the present invention to provide a new and improved active fixation mechanism for cardiac stimulating electrodes.

Examples of active fixation mechanisms heretofore proposed include the following. U.S. Patent No. 3,943,936 to Rasor et al., assigned to the same assignee as is the present invention, discloses various means for attaching the stimulating electrode to the myocardium, including spiral retention wires and wire barbs. U.S. Patent Nos. 4,142,530 to Wittkampf, 4,217,913 to Dutcher, and 4,357,946 to Dutcher et al. describe stylet-actuated anchoring means including hooks and corkscrews for catheter electrodes. U.S. Patent No. 4,378,023 to Trabucco discloses anchoring mechanisms in the form of normally recessed pins and hooks which are stylet-deployable to engage the tissue and anchor the electrode. Similarly, U.S. Patent No. 4,233,992 to Bisping describes various forms of fixing hooks normally recessed within the contour of the electrode head for ease of insertion through the vein to place the electrode into desired position, and stylet-pivotable to protrude beyond the electrode head such that upon twisting the lead, the hook engages the heart tissue. Bisping further suggests that the fixing hook or the electrode head be provided with barbs to prevent disengagement of the hook, and also describes alternatives to stylet actuation of the fixing hook.

A serious problem with many of the previous approaches toward active fixation of the lead/electrode is that the anchoring means is permanently deployed, or is not easily retracted to its original position after deployment. Thus, while it may be relatively easy to thread the lead through the vein and position the stimulating electrode in place in the chamber, it becomes quite difficult to remove or reposition the lead without possible severe trauma to surrounding tissue of the heart and/or the entry vein. This is a serious obstacle to even slight repositioning of the electrode once affixed, such as the surgeon might attempt if, as sometimes happens, the threshold for the anchored electrode is considerably higher than was observed just prior to the "permanent" fixation.

Accordingly, it is another object of the present invention to provide an active fixation mechanism for a catheter lead, which may be removed from one fixation location to another without serious injury to nearby or underlying tissue.

SUMMARY OF THE INVENTION

Briefly, the active fixation mechanism of the present invention is positioned within the general confines of the lead body for selective deployment by the surgeon after lead insertion and placement of the electrode in what appears, based on capture observations and threshold measurement, to be the optimum location for stimulation. According to a principal feature of the present invention, the electrode is readily repositioned after it has been affixed, by simply removing the fixation mechanism from the tissue for retraction to its original position within the confines of the lead body, or, if more convenient, by removal from the tissue and redeployment to a new noninterfering position. In this way, the electrode may either be relocated adjacent excitable myocardial tissue within the selected chamber, or for the lead may be partially or complete withdrawn, without inflicting serious injury on cardiac tissue or the vascular system.

In a preferred embodiment of the invention, the active fixation mechanism comprises a rigid hook insulated from the electrode and adapted to be manipulated into engagement with tissue in the vicinity of the electrode. The mechanism includes spring means for biasing the hook into an initial position within or substantially within the periphery of the lead, and further means for selectively overcoming the bias to move the hook into tissue-engaging position. The hook is also movable to a separate noninterfering override position for withdrawal of the lead.

According to the latter aspect of the invention, the hook is adapted to permit its movement into the override position if, for example, tissue growth occurring after implantation of the electrode prevents retraction of the hook to its initial position. In that event, a slight tug on the lead will cause the hook to rotate about its pivot point to a position beyond the tip, thereby allowing the lead to be withdrawn.

BRIEF DESCRIPTION OF THE DRAWINGS

The foregoing and still further objects, features and attendant advantages of the present invention will become apparent from careful consideration of the ensuing detailed description of a presently preferred embodiment, taken in conjunction with the accompanying drawings in which:

FIG. 1 is a side view of the distal end of a lead assembly for an implantable cardiac pacemaker according to the preferred embodiment, partly in section through the longitudinal axis of the lead assembly;

FIG. 2 is a sectional view of the lead assembly taken along the line 2—2 of FIG. 1; and FIG. 3 is a view of the lead assembly looking toward the distal end.

DETAILED DESCRIPTION OF THE PREFERRED EMBODIMENT

Referring now to FIGS. 1 and 2, a currently preferred embodiment of an active fixation mechanism according to the present invention is provided in conjunction with the electrode assembly at the distal end of a lead 10 for use with a cardiac pacemaker. Except as will otherwise be described herein, the lead 10 is of generally conventional construction. The lead shown in the FIGS. is configured for unipolar stimulation of the heart, but the structure and operation of the active fixation mechanism embodiment to be described is usable irrespective of whether the mode of stimulation is unipolar or bipolar. Further, it will be understood that although the preferred embodiment of the invention is described in the context of a cardiac pacemaker, the invention may be employed in any environment in which a lead or electrode is to be secured to tissue accessible via the vascular system.

At its distal end, the lead 10 includes a stimulating cathodic electrode 12 having a necked-down, generally tubular configuration disposed at the periphery of the lead and spaced slightly back from the tip. According to the invention, cathode 12 is configured and positioned to cooperate with an active fixation mechanism 15, to be described in detail presently. Cathode 12 may be fabricated from any material or materials conventionally employed for cardiac stimulating electrodes, such as titanium or platinum-iridium alloy, but is preferably composed of a titanium substrate coated on its exposed surface 17 with a thin layer of iridium oxide, in the manner described in copending U.S. patent application Ser. No. 838,607 of Ross G. Baker, Jr., entitled "Low Threshold Cardiac Pacing Electrodes", filed March 11, 1986, new patent no. 4,679,572 and assigned to the same assignee as is the present invention.

Cathode 12 is electrically connected to a conductive coil 20 which extends the entire length of the lead 10 and terminates in a male connector (not shown) for mating with a female connector built-in to the case housing the pulse generator. The electrical connection between cathode 12 and coil 20 is facilitated as follows. The inner surface of the cathode tube is firmly seated against the outer surface of an axially-extending type-316 stainless steel mounting sleeve 22. An uninsulated portion of the coil 20 is wound tightly about a smaller diameter section of mounting sleeve 22, and is sandwiched between the sleeve and the inner surface of a type-316 stainless steel tube 25. The latter tube is crimped at locations 28 to provide a tight electrical connection between coil 20 and mounting sleeve 22, and thereby, with cathode 12.

The coil 20 and the other elements providing the connection with cathode 12 are covered with an insulative sleeve 29, composed of a conventional biocompatible material such as polyurethane, which abuts against one end of the cathode. The tight seating of cathode 12 on mounting sleeve 22 is assured by an interference fit between the two, thereby providing a firm mechanical as well as electrical connection therebetween. In addition, the insulative sleeve may be fastened tightly against the cathode at the abutting seam by use of a conventional biocompatible medical grade adhesive, such as Dow Medical Adhesive Silicone Type A, to prevent entry of body fluid at the seam to the interior of the lead 10.

At its other end, cathode 12 is seated against and retained on a rigid, electrically insulative, generally cylindrical member 30 which terminates the lead 10 at tip 31. Member 30 is the housing for the active fixation mechanism of the present invention, and is referred to hereinafter as the fixation assembly head. It may be composed of any conventional biocompatible electrically insulating material suitable for use in catheter leads, such as polyurethane or Delrin. Preferably, however, fixation assembly head 30 is composed of Celcon (a trademark of the Celanese Corporation for its brand of acetal polymer), because that material flows more easily and is more readily molded than the aforementioned other exemplary materials.

Fixation assembly head 30 is molded in two separate piece parts 33 and 34, which mate together along a tongue-in-groove fitting 32. The mated assembly head snaps into the space between cathode 12 and mounting sleeve 22 for secure retention therein, as well as for maintaining the mating relationship between its two piece parts. The piece parts 33 and 34 are additionally held together by a band 35 composed, for example, of stainless steel or titanium. The seam between the two may further be rendered impervious to body fluid by cementing piece parts 33 and 34 together with medical grade adhesive.

Piece parts 33 and 34 are individually molded such that when they are mated together they form an internal cavity 37 shaped to retain and permit operation of the principal parts of the active fixation mechanism 15 according to the present invention. In particular, the active fixation mechanism includes a rigid hook 36 which is bent with several angles to form a generally U-shaped segment comprising legs 38 and 40, with leg 38 extending into the arcuate portion of hook 36 and terminating in a sharp tip 51. Hook 36 is arranged to pivot about the axis of leg 38 which is retained adjacent a rounded corner of cavity 37 by a coil spring 39 lying directly against that corner and encompassing a segment of leg 38. Leg 40 of the hook is confined to an arcuate channel 41 of cavity 37, and may have a roller sleeve 43 thereon for ease of movement.

Coil spring 39 has a pair of legs 42 and 44, leg 42 being forced against an angled wall of cavity 37, and leg 44 extending against and partially encircling leg 40 of the hook, whereby leg 40 is urged against one end of channel 41. Hence, the construction and arrangement is such that hook leg 40 may undergo rotation through the arcuate channel 41, about the axis of leg 38, when sufficient force is exerted against leg 40 in an axial direction toward lead tip 31 to overcome the bias of coil spring 39. Fixation assembly head 30 is provided with a rounded outer wall 57 deviating from its otherwise cylindrical shape, to give it desirable additional wall thickness in the region of the rounded corner of the internal cavity 37 adjacent which hook leg 38 is constrained. Both hook 36 and coil spring 39 are preferably composed of MP35N alloy (an alloy comprising nickel, cobalt, chromium, and molybdenum) manufactured by Maryland Specialty Wire Company (Cockeysville, Maryland 21030).

The sharp pointed tip 51 of hook 36 rotates together with hook leg 40 about the axis of hook leg 38, and through the same angle (circumscribed by the arcuate channel 41). When hook leg 40 is constrained to its normal position against the end of arcuate channel 41 closest to cathode 12, as a result of the urging by coil spring 39, tip 51 of hook 36 is biased (by the same spring force) into a recess 53 formed by the necked-down region of cathode 12, as indicated at position X—X of leg 40 and hook 36 in FIG. 1 and by the phantom showing of the hook and tip 51 in FIG. 2. Thus, the hook is normally substantially confined within the boundary or periphery of the lead 10 as viewed from the tip or side of the distal end of the lead. In that position, the bottom portion of the U-shaped segment between hook legs 38 and 40 slides back against the wall of a cutout 52 within cavity 37, such that no portion of the hook projects significantly beyond the periphery of the lead 10.

Lead 10 is provided with a conventional stylet 55 movable in a conventional manner longitudinally back and forth along an axial opening in the lead, formed in this instance by conductive coil 20 and the aligned central hole in mounting sleeve 22 and in fixation assembly head 30, under the guidance and control exerted by the implanting surgeon from the exposed end of the lead. Thereby, the stylet may be pushed into and withdrawn from the internal cavity 37 in the fixation assembly head at will.

In operation, the lead is inserted through the superior vena cava to position the exposed surface of the stimulating electrode 12 in the selected chamber of the heart in a location of low threshold measurement in proximity to excitable myocardial tissue. When the implanting physician is satisfied that this appears to represent the best location for the stimulating electrode, the stylet 55 is pushed into contact with hook leg 40, which lies across the central hole and thus interferes with continued movement of the stylet into cavity 37. Continued exertion of axial force on the stylet will cause the spring 39 to flex as the bias it exerts is overcome, thereby pivoting leg 40 and, with it, hook 36 about the axis of leg 38. Hook tip 51 moves from its initial recessed position X—X into the tissue-engaging position represented by the locations A—A of leg 40 and hook 36 in FIG. 1 and by the sectional view for the A—A location in FIG. 2

In the preferred embodiment, the radius of the cylindrical portion of fixation assembly head 30 at lead tip 31 is only about 0.040 inch, and the hook tip 51 is separated approximately 0.040 inch from the immediately adjacent surface of the head when leg 40 and hook 36 are in the A—A position, so there is not a great deal of space required for arcuate movement of the hook. At that point, a clockwise twist of the lead through an angle less than 90 degrees will suffice to cause the hook tip 51 to engage tissue in proximity thereto in the chamber, thereby securing the electrode in place at the desired site. The stylet may then be withdrawn, without affecting the anchoring of the electrode.

The position A—A of the hook depicted in FIG. 1 is that which would be assumed using a 0.014 inch diameter stylet. If, instead, a 0.016 inch diameter stylet were used, the hook tip 51 would be positioned further toward the tip 31 of lead 10 as shown by the position B—B of leg 40 and hook 36. Both stylet sizes are conventionally utilized for catheter-type pacemaker leads, and hence, the central hole in the lead may be of sufficient diameter to accommodate either stylet size.

If it is desired to relocate the electrode or to withdraw the lead at or after the time of implant, the surgeon need merely twist the lead counterclockwise, thereby disengaging the hook tip 51 from the adjacent tissue. The force exerted by the coil spring 39 will then return the hook tip to its normal restrained position X—X (FIG. 1) within recess 53. The electrode may then be repositioned as desired, the lead may be withdrawn from the vein.

The hook tip may be moved into an override position (designated by C—C of FIG. 1) if, after the lead is rotated to withdraw the hook from tissue, it remains obstructed. To that end, the surgeon may pull slightly on the exposed proximal end of the lead to force the hook 36 further against the force exerted by the coil spring 39 until the force exerted by the coil spring is completely overridden. With the hook tip dislodged in this manner, the lead is readily repositioned or withdrawn. Upon movement of the electrode to a new location, the hook is free to be returned to its original restrained position in cavity 53 unless repositioned using the stylet.

FIG. 3 is an end view of the lead 10 with the hook 36 in the override position (C—C of FIG. 1). The availability of an override position is useful when, after a period of time, the hook tip may be caught by fibrotic growth after being twisted out of engagement with the cardiac tissue, or is otherwise lodged to prevent return to its normal restrained position in the cavity. Longitudinal movement of the lead with the hook tip in extended position (such as A—A or B—B of FIG. 1) could result in injury to the myocardium, a valve or to the lining of the vein. The capability of the hook tip to be brought to the override position (C—C), in which it is out of the way and unlikely to engage tissue during removal of the lead, is an important aspect of the invention.

Although a specific presently preferred embodiment of the invention has been described, it will be apparent to those of ordinary skill in the field to which the invention pertains from a consideration of the foregoing description and drawings that variations and modifications may be made without departing from the spirit and scope of the invention. Accordingly, it is intended that the invention be limited only to the extent required by the appended claims.

What is claimed is:

1. An active fixation mechanism adapted to secure a stimulating electrode to tissue to be stimulated, said electrode being fixed to the distal end of an endocardial lead, said fixation mechanism comprising:

a generally cylindrical housing extending axially of said lead beyond said electrode;

a rigid hook having a first end pivotally coupled to the housing and a second end adapted to move between a first concealed position within said housing and a second exposed position encompassing at least a portion of said housing and spaced therefrom wherein axial rotation of said lead causes said hook to engage cardiac tissue in the vicinity of the electrode;

spring means biasing the hook to said first position; and means for selectively overcoming the bias of the spring means for moving the hook into said tissue-engaging second position.

2. The active fixation mechanism according to claim 1, wherein said spring means biases the hook in a first direction, said bias being overcome in the opposite direction such that the hook is movable to a third position projecting beyond the distal end of the lead, in which position the hook is not likely to engage tissue during withdrawal of the lead.

3. An active fixation mechanism for a pacemaker lead having a tissue-stimulating electrode fixed to the distal end thereof, said fixation means comprising:

a housing of insulative material extending coaxially beyond said electrode;

tissue-engaging means movably fastened to said housing;

a recess in said housing adjacent the distal end thereof;

resilient means urging said tissue-engaging means to a first position substantially within said recess; and means for overcoming said resilient means to move at least a portion of said tissue-engaging means to a second position extending outwardly of said lead encompassing at least a portion of said housing wherein axial rotation of said lead causes engagement of tissue by said tissue-engaging means.

4. The active fixation mechanism according to claim 3, wherein said resilient means is adapted to be overcome by application of sufficient force to said tissue-engaging means to cause said tissue-engaging means to assume a third position extending beyond the distal end of said lead in which third position it is precluded from engaging tissue.

5. The active fixation mechanism according to claim 3, wherein said tissue-engaging means has a first portion normal to the axis of said housing, and an integral hook portion having a sharp tip received in said recess in said first position, said hook extending from said housing in spiral fashion in said second position.

6. A fixable tissue-stimulating electrode and lead for a cardiac stimulator, comprising:

housing means of insulative material fixed on the distal end of said lead;

anchoring means movable positioned on said housing adapted to fix the electrode of said lead relative to excitable cardiac tissue;

means biasing said anchoring means to normally lie substantially within said housing means;

means for moving said anchoring means outwardly of said housing from a first concealed position to a second position in tissue-engaging relationship with respect to said excitable tissue, said tissue being engaged by rotation of said lead about its axis.

7. The fixable tissue-stimulating electrode and lead according to claim 6, wherein said means for moving said anchoring means includes stylet means adapted to pass axially through said lead to exert a force on said anchoring means overcoming said bias means and drive said anchoring means into said second position.

8. The fixable tissue-stimulating electrode and lead according to claim 7, wherein said housing defines a cavity configured to receive said anchoring means therein.

9. The fixable tissue-stimulating electrode and lead according to claim 8, wherein said anchoring means comprises a rigid hook having one end fastened for rotation on said housing relative to the electrode.

10. The fixable tissue-stimulating electrode and lead according to claim 9, wherein said resilient means comprises a spring rotatably urging said hook to a normal position within said cavity.

* * * * *